(12) United States Patent
Fry et al.

(10) Patent No.: US 8,338,402 B2
(45) Date of Patent: Dec. 25, 2012

(54) SCAFFOLD

(75) Inventors: Nicholas Fry, York (GB); Anthony Dagger, York (GB); David Morsley, York (GB); Helene Lecomte, York (GB); Roy Trayhern, York (GB); Mark Howard, York (GB); Sarah Freestone, York (GB); Brian Thomson, York (GB); Mark Smith, York (GB); Rebecca Crallan, York (GB)

(73) Assignee: Smith & Nephew PLC, London (GB)

( * ) Notice: Subject to any disclaimer, the term of this patent is extended or adjusted under 35 U.S.C. 154(b) by 679 days.

(21) Appl. No.: 12/300,636

(22) PCT Filed: May 10, 2007

(86) PCT No.: PCT/GB2007/001713
§ 371 (c)(1),
(2), (4) Date: Sep. 29, 2009

(87) PCT Pub. No.: WO2007/132186
PCT Pub. Date: Nov. 22, 2007

(65) Prior Publication Data
US 2010/0297208 A1    Nov. 25, 2010

(30) Foreign Application Priority Data

May 12, 2006 (GB) .................................. 0609455.1
Feb. 14, 2007 (GB) .................................. 0702846.7

(51) Int. Cl.
*A61K 31/585* (2006.01)
*A61K 31/19* (2006.01)
*A61L 15/00* (2006.01)
*C08G 63/08* (2006.01)

(52) U.S. Cl. ......... 514/175; 514/557; 424/445; 528/354
(58) Field of Classification Search ................. 514/557, 514/175; 424/445; 528/354
See application file for complete search history.

(56) References Cited

U.S. PATENT DOCUMENTS

| | | |
|---|---|---|
| 1,975,504 A | 10/1934 | Formhals |
| 2,280,915 A | 4/1941 | Johnson |
| 2,910,763 A | 8/1955 | Lauterbach |
| 4,184,510 A | 1/1980 | Murry et al. |
| 4,294,240 A | 10/1981 | Thill |
| 4,316,466 A | 2/1982 | Babb |
| 4,418,691 A | 12/1983 | Yannas et al. |
| 4,664,662 A | 5/1987 | Webster |
| 4,792,328 A | 12/1988 | Beck et al. |
| 4,841,961 A | 6/1989 | Burlage et al. |
| 4,841,962 A | 6/1989 | Berg et al. |
| 4,929,477 A | 5/1990 | Will |
| 4,936,834 A | 6/1990 | Beck et al. |
| 5,073,172 A | 12/1991 | Fell |
| 5,267,952 A | 12/1993 | Gardner |
| 5,380,280 A | 1/1995 | Peterson |
| 5,489,304 A | 2/1996 | Orgill et al. |
| 5,636,643 A | 6/1997 | Argenta et al. |
| 5,645,081 A | 7/1997 | Argenta et al. |
| 5,716,411 A | 2/1998 | Orgill et al. |
| 5,759,570 A | 6/1998 | Arnold |
| 5,795,584 A | 8/1998 | Totakura et al. |
| 6,673,029 B1 | 1/2004 | Watson |
| 6,695,824 B2 | 2/2004 | Howard et al. |
| 6,752,794 B2 | 6/2004 | Lockwood et al. |
| 6,942,628 B1 | 9/2005 | Watson |
| 7,070,584 B2 | 7/2006 | Johnson et al. |
| 7,182,758 B2 | 2/2007 | McCraw |
| 7,381,859 B2 | 6/2008 | Hunt et al. |
| 7,534,240 B1 | 5/2009 | Johnson |
| 7,534,859 B2 | 5/2009 | Messing et al. |
| 7,763,769 B2 | 7/2010 | Johnson et al. |
| 7,790,945 B1 | 9/2010 | Watson, Jr. |
| 7,828,782 B2 | 11/2010 | Suzuki |
| 2001/0034499 A1 | 10/2001 | Sessions et al. |
| 2001/0043943 A1 | 11/2001 | Coffey |
| 2003/0050590 A1 | 3/2003 | Kirsch |
| 2003/0050594 A1 | 3/2003 | Zamierowski |
| 2003/0108587 A1 | 6/2003 | Orgill et al. |
| 2003/0144619 A1 | 7/2003 | Augustine |
| 2003/0171675 A1 | 9/2003 | Rosenberg |
| 2003/0211130 A1* | 11/2003 | Sanders et al. ................ 424/423 |
| 2003/0225347 A1 | 12/2003 | Argenta et al. |
| 2004/0054338 A1 | 3/2004 | Bybordi et al. |
| 2004/0073151 A1 | 4/2004 | Weston |

(Continued)

FOREIGN PATENT DOCUMENTS

DE    198 44 355    4/2000

(Continued)

OTHER PUBLICATIONS

Mikos et al., Journal of Biomedical Materials Research, 11993, 27, 183-189.*

(Continued)

*Primary Examiner* — Abigail Fisher
(74) *Attorney, Agent, or Firm* — Knobbe, Martens, Olson & Bear LLP (57) ABSTRACT

The present invention relates to scaffolds which can be used as medical devices for guided tissue regeneration and repair, in particular the invention is directed to a scaffold comprising fibers having a mean fiber diameter of between from about 1.2 to 4.0 microns, wherein the fibers comprise a glycolide. The invention further relates to the use of the scaffolds for the selective capture of cell populations for a cell source material.

20 Claims, 6 Drawing Sheets

U.S. PATENT DOCUMENTS

| | | | |
|---|---|---|---|
| 2005/0065484 A1 | 3/2005 | Watson, Jr. | |
| 2005/0209574 A1 | 9/2005 | Boehringer et al. | |
| 2005/0222544 A1 | 10/2005 | Weston | |
| 2005/0234485 A1 | 10/2005 | Seegert et al. | |
| 2006/0189910 A1 | 8/2006 | Johnson et al. | |
| 2007/0027414 A1 | 2/2007 | Hoffman et al. | |
| 2007/0066945 A1 | 3/2007 | Martin | |
| 2007/0185426 A1 | 8/2007 | Ambrosio et al. | |
| 2007/0185463 A1 | 8/2007 | Mulligan | |
| 2007/0219471 A1 | 9/2007 | Johnson et al. | |
| 2007/0225663 A1 | 9/2007 | Watt et al. | |
| 2007/0293830 A1 | 12/2007 | Martin | |
| 2008/0107711 A1 | 5/2008 | Shelokov | |
| 2008/0114277 A1 | 5/2008 | Ambrosio et al. | |
| 2008/0199513 A1 | 8/2008 | Beretta et al. | |
| 2008/0234641 A1 | 9/2008 | Locke et al. | |
| 2009/0005796 A1 | 1/2009 | Swain | |
| 2009/0093550 A1 | 4/2009 | Rolfes et al. | |
| 2009/0105671 A1 | 4/2009 | Daggar et al. | |
| 2010/0100022 A1 | 4/2010 | Greener et al. | |
| 2010/0143435 A1* | 6/2010 | Dagger et al. | 424/422 |
| 2010/0268176 A1 | 10/2010 | Johnson et al. | |
| 2011/0015586 A1 | 1/2011 | Orgill et al. | |

FOREIGN PATENT DOCUMENTS

| | | |
|---|---|---|
| EP | 0020662 B1 | 7/1984 |
| EP | 1 614 789 | 1/2006 |
| FR | 1 163 907 | 10/1958 |
| GB | 114754 | 4/1918 |
| GB | 641061 | 8/1950 |
| GB | 821959 A | 10/1959 |
| GB | 1 224 009 A | 3/1971 |
| GB | 1549756 A | 8/1979 |
| GB | 2195255 A | 4/1988 |
| GB | 2378392 A | 2/2003 |
| JP | S63-264073 | 10/1988 |
| WO | WO 90/10424 | 9/1990 |
| WO | WO 90/11795 | 10/1990 |
| WO | WO 91/00718 | 1/1991 |
| WO | WO 92/20299 | 11/1992 |
| WO | WO 94/20041 | 9/1994 |
| WO | WO 00/07653 | 2/2000 |
| WO | WO 02/083046 A1 | 10/2002 |
| WO | WO 02/092783 | 11/2002 |
| WO | WO 03/026544 | 4/2003 |
| WO | WO 03/072748 | 9/2003 |
| WO | WO03/094811 A | 11/2003 |
| WO | WO 03/101385 | 11/2003 |
| WO | WO 2004/024300 | 3/2004 |
| WO | WO 2004/037334 | 5/2004 |
| WO | WO 2004/112850 | 12/2004 |
| WO | WO 2005/046761 | 5/2005 |
| WO | WO 2005/046762 | 5/2005 |
| WO | WO 2005/051461 | 6/2005 |
| WO | WO 2005/070480 | 8/2005 |
| WO | WO 2006/005939 | 1/2006 |
| WO | WO 2006/009853 | 1/2006 |
| WO | WO 2006/028244 | 3/2006 |
| WO | WO 2006/046060 A | 5/2006 |
| WO | WO 2006/099137 | 9/2006 |
| WO | WO 2008/005532 | 1/2008 |
| WO | WO 2008/141228 A1 | 11/2008 |
| WO | WO 2009/088926 A1 | 7/2009 |

OTHER PUBLICATIONS

You et al., Journal of Applied Polymer Science, 2005, 95, 193-200.*

U.S. Appl. No. 12/443,169, submitted Mar. 26, 2009, including its ongoing prosecution history, including without limitation Office Actions, Amendments, Remarks, and any other potentially relevant documents, Apr. 15, 2004, Weston.

Application for Modification to HCPCS Level II Code Set in the 2005-2006 Coding Cycle. www.cms.hhs.gov/medicare/hcpcs/.

Boland et al., "Tailoring Tissue Engineering Scaffolds Using Electrostatic Processing Techniques: A Study of Poly(Glycolic Acid) Electrospinning" Journal of Macromolecular Science A. Pure and Applied Chemistry, A38(12), 1231-1243 (2001).

Boland E.D. et al. Utilizing acid pre-treatment and electrospinning to improve biocompatibility poly(glycolic acid) for tissue engineering. J. Biomed. Mater. Res. Part B: Appl Biomater 71B 144-152, 2004.

Boretos, John, "Cellular Polymers for Medical Use: The Vital Role of Porosity and Permeability," Cellular Polymers 3 (1984) 345-358.

Chardack et al., "Experimental Studies on Synthetic Substitutes for Skin and Their Use in the Treatment of Burns," Annals of Surgery, Jan. 1962, pp. 127-139.

Chariker, M.E., et al, "Effective Management of Incisional and Cutaneous Fistulae with Closed Suction Wound Drainage," Contemporary Surgery. Jun. 1989, pp. 59-63, vol. 34 USA.

Database WPI Week 200624, Derwent Publication Ltd., London, GB; AN 2006-231788, XP002456707.

Dilmaghani et al., "A Method for Closed Irrigation and Suction Therapy in Deep Wound Infections," Journal of Bone and Joint Surgery, 1969, vol. 51-A, No. 2, pp. 323-342.

Greene, M. A., et al. Laparotomy Wound Closure with Absorable Polyglycolic Acid Mesh, Surgery, Gynecology and Obsterics 1993; 176: 213-218, Mar. 1993.

Grover et al., "Recent Advances: Plastic Surgery," BMJ, 1998, vol. 317, August, www.bmj.com.

Hartz, R.S., et al., Healing of the Perineal Wound, Arch. Surg., Apr. 1980, 115, 471-474.

International Search Report for International Application No. PCT/GB2006/004379 date of mailing Apr. 12, 2007 in 4 pages.

International Search Report from PCT/GB2007/001713 mailed Dec. 11, 2007.

Ma, Peter X. Scaffolds for tissue fabrication. Materials Today, Review, May 2004.

Middleton, J., A. Tipton (Mar. 1998). "Synthetic biodegradable polymers as medical devices" (HTML). Medical Plastics and Biomaterials Magazine.

Miller, et al., "Treating a Postoperative, Ischemic Foot Wound Using Bovine Dermal-Derived Extra-cellular Matrix PRIMATRIX™ with The BlueSky Medical Versative 1TM Negative Pressure Wound Therapy System," The Wound Healing Center, Terre Haute, Indiana, Stirling Clinic, Indianapolis, IN.

NURSING75, Wound Suction: Better Drainage with Fewer Problems, Nursing, vol. 5, No. 10, Oct. 1875, pp. 52-55.

Reedy, Justin, "The Science Behind Wound Healing," UW Health Sciences, 2004-2005.

Schein et al., "The 'Sandwich Technique' in the Management of the Open Abdomen," British Journal of Surger, 1986, vol. 73, May, pp. 369-370.

Stewart, Joanne, Ph.D., World Wide Wounds—Next generation of products for wound management—2002 (13 pages).

Svedman, P., "Irrigation Treatment in Split-Thickness Skin Grafting of Intractable Leg Ulcers," Scand J. Plast. Reconst. Surg., 19:211-213, 1985.

Svedman, P., "Irrigation Treatment of Leg Ulcers," The Lancet, Sep. 1983, 532-34.

Svedman, P., A Dressing Allowing Continuous Treatment of a Biosurface, IRCS Med. Science: Biomed. Tech.; Clinic. Med.; Surg. and Transplantation, 1979, 7, p. 221.

Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133.

Swift, et al, "Quorum Sensing in *Aeromonas hydrophila* and *Aeromonas salmoncida*: Identification of LuxRI Homologs AhyRI and AsaRI and Their Cognate N-Acylhomoserine Lactone Signal Molecules," J. Bacteriol., 179(17):5271-5281 (1997).

Teder and Svedman et al., "Continuous Wound Irrigation in the Pig," Journal of Investigative Surgery, 1990, vol. 3, pp. 399-407.

Thomas, Stephen Wound Management and Dressings 35-42 (1990).

Tribble, David E. M.D., An Improved Sump Drain-Irrigation Device of Simple Construction, Archives of Surgery New York, pp. 511-13, 1972 vol. 105.

Westaby, S., et al., "A Wound Irrigation Device", The Lancet, Sep. 2, 1978, pp. 503-504.

Wooding-Scott, Margaret, et al., "No Wound is Too Big for Resourceful Nurses," RN Dec. 1988, pp. 22-25 USA.

Alexander, J. Wesley, et al., "Clinical Evaluation of Epigard, A New Synthetic Substitute for Homograft and Heterograft Skin," The Journal of Trauma, vol. 13, No. 4, 1973, pp. 374-383.

Chinese First Office Action dated May 26, 2010 for Chinese Application No. 200780025215.7 (9 pages).

Chinese Third Office Action dated Mar. 23, 2011 for Chinese Application No. 200780025215.7, (9 pages).

European First Office Action dated Jul. 23, 2009 for European Application No. 07732741.9, (5 pages).

European Second Office Action dated Jun. 1, 2010 for European Application No. 07732741.9, (5 pages).

European Third Office Action dated Jul. 8, 2011 for European Application No. 07732741.9, (4 pages).

Mikos et al., "Preparation of Poly (glycolic acid) Bonded Fiber Structures for Cell Attachment and Transplantation," Journal of Biomedical Materials Research, 1993, vol. 27, pp. 183-189.

Vijanto, J. and J. Raekallio, "Local Hyperalimentation of Open Wounds," Br. J. Surg., 1976, vol. 63, pp. 427-430.

You et al., "In Vitro Degradation Behavior of Electrospun Polyglycolide, Polylactide, and Poly (lactide-co-glycolide)," Journal of Applied Polymer Science, 2005, vol. 95, pp. 193-200.

First Japanese Office Action (w/English translation) dated Sep. 25, 2012 for Japanese Patent Application No. 2009-508489 (9 pages).

A.S. Badami et al., "Effect of fiber diameter on spreading, proliferation, and differentiation of osteoblastic cells on electrospun poly (lactic acid) substrates," Biomaterials, vol. 27, No. 4, Feb. 2006, pp. 596-606, Elsevier Science Publishers B.V., United Kingdom.

Takao Nishimura, "Development of Leukocyte Removal Filter from Microfiber Non-Woven Cloth," Polymer Processing, vol. 52, No. 2, Feb. 25, 2003, pp. 76-81.

* cited by examiner

SECTION A-A
SCALE 1 : 1

SCAFFOLD

CROSS-REFERENCE TO RELATED APPLICATIONS

This Application is a U.S. National Phase of International Application No. PCT/GB2007/001713 filed May 10, 2007, designating the United States and published on Nov. 22, 2007, as WO 2007/132186, which claims the priority of Great Britain Provisional Patent Application No. 0609455.1, filed May 12, 2006, and Great Britain Provisional Patent Application No. 0702846.7, filed Feb. 14, 2007, the entire contents of all of which are hereby incorporated by reference.

BACKGROUND OF THE INVENTION

1. Field of the Invention

The invention relates to scaffolds which can be used as medical devices for guided tissue regeneration and repair and for the selective capture of cell populations from a cell source material.

2. Description of the Related Art

Scaffold technologies are known for use in dermal regeneration in chronic and acute wounds. A number of these technologies exploit the biological properties of relatively pure natural polymers such as collagen, silk, alginate, chitosan and hyaluronate extracted from animal or plant tissue. Others are based upon processed extracellular matrix (decellularized) materials which contain multiple natural macromolecules. An example of such a scaffold is Oasis® (Healthpoint Limited), a biologically derived extracellular matrix-based wound product comprised of porcine-derived acellular small intestine submucosa which contains type I collagen, glycosaminoglycans and some growth factors.

However, there are concerns over the use of natural polymers because of the potential pathogen transmission, immune reactions, poor handling, mechanical properties and less controlled biodegradability[1].

The technique of electrospinning was first introduced in the early 1930's to fabricate industrial or household non-woven fabric products. In recent years, the technique has been utilised to form scaffolds of polymer fibres for use in tissue engineering. The technique involves forcing a natural or synthetic polymer solution through a capillary, forming a drop of the polymer solution at the tip and applying a large potential difference between the tip and a collection target. When the electric field overcomes the surface tension of the droplet, a polymer solution jet is initiated and accelerated towards the collection target. As the jet travels through the air, the solvent evaporates and a non-woven polymer fabric is formed on the target. Such fibrous fabrics, having an average fibre diameter in the micrometer or nanometer scale, have been used to fabricate complex three-dimensional scaffolds for use in tissue engineering applications.

It is widely accepted within the scientific community that scaffolds having fibres of a small diameter result in the greatest biological response, as evidenced by measuring cell adhesion and proliferation. This is considered to be as a result of the fibres providing a large surface area to which the cells can adhere and subsequently proliferate. As a strong correlation exists between fibre diameter and pore size, any scaffold having fibres of a small diameter will be also characterised by small pore size. This will however have a negative effect on the migration of the cells into the scaffold, potentially leading to a restricted regeneration of replacement tissue around the periphery of the scaffold, with the core of the scaffold being substantially acellular.

An unanticipated problem associated with many of the known electrospun scaffolds is that they become dimensionally unstable when incubated in aqueous solution at body temperature. This instability is measurable both macroscopically by scaffold shrinkage and microscopically by loss of initial fibrous architecture and reduction in initial pare size. Dimensionally unstable scaffolds will be of minimal use as their shrinkage can potentially have a significant impact on the behaviour of the scaffold and its interaction with the cellular environment.

SUMMARY

Surprisingly, we have identified scaffolds having an architecture that is optimal for cell adhesion, proliferation and migration whilst also demonstrating dimensional stability over the time required for these initial cellular processes.

Blood contains various specialised cell types which are classified into: erythrocytes, leukocytes and platelets. A primary function of platelets, also referred to as thrombocytes, is hematostasis. Platelets release a number of factors into the blood including ECM proteins and cytokines such as growth factors and other proinflammatory factors like serotonin, bradykinin, prostaglandins, prostacyclins, thromboxane, and histamine, thereby increasing cell proliferation and migration to the area and causing blood vessels to become dilated and porous.

Local administration of certain cell types has been shown to be more effective than the local administration of exogenous factors. Therefore in certain circumstances it may be desirable to selectively recover a particular therapeutically beneficial subset of cells from a blood sample. For example, it may be desirable to selectively isolate and recover the platelet population from a blood sample in order that an exogenous source of platelets can be immediately provided at a wound site to enhance the bodies inherent repair mechanism.

Additionally, scaffolds implanted without cells do not demonstrate the same structural integrity as cell-seeded devices. This results in a prolonged period until the device is truly functional, during which time it may fail.

Whilst in some medical and/or surgical applications of the scaffold it may be satisfactory for cell migration to occur post-implantation, in other circumstances it may desirable to implant the scaffold already containing cells.

A known process of seeding a scaffold is to culture the scaffold with a cell population within a bioreactor, thereby allowing the cells to gradually infiltrate the scaffold. However, the use of bioreactors is expensive, technically challenging and takes many weeks to produce the final product.

Attempts at injecting cells directly into pre-implanted scaffolds does not lead to suitable distribution throughout the scaffold resulting in a loss of function.

We have found that the scaffold of the present invention in addition to demonstrating optimal geometry for cell adhesion, proliferation and migration post-implantation can also be used within a cell capturing device to preferentially capture specific populations of cells from a sample.

The scaffold of the present invention selectively captures the platelet population from a blood sample having a platelet density of about 200000-300000/mm$^3$. The erythrocytes are not selectively captured. This selection is particularly surprising as the diameter of a platelet is about 2-3 μm and the diameter of an erythrocyte is about 6-8 μm. This scaffold seeded with platelets can be implanted into a medical and/or surgical site.

The scaffold of the present invention also selectively captures the leukocyte population from a blood sample having a leukocyte density of about 5000-7000/mm. The erythrocytes are not selectively captured.

BRIEF DESCRIPTION OF THE DRAWINGS

The invention is herein described, by way of example only, with reference to the accompanying Figures.

DETAILED DESCRIPTION OF THE PREFERRED EMBODIMENTS

According to an aspect of the invention there is provided a scaffold comprising fibres having a mean fibre diameter of between from about 1.2 to 4.0 microns, and wherein said fibres comprise a glycolide.

In embodiments of the invention the mean fibre diameter is between from about 1.3 to 2.9 microns. In further embodiments of the invention the mean fibre diameter is between from about 1.5 to 3.5 microns and more particularly between from about 1.9 to 2.6 microns.

In embodiments of the invention the fibre comprises over 90% polymer, over 95% polymer or consists of 100% polymer.

The polymers used in the present invention can be natural, synthetic, biocompatible and/or biodegradable.

The term "natural polymer" refers to any polymers that are naturally occurring, for example, silk, collagen-based materials, chitosan, hyaluronic acid and alginate.

The term "synthetic polymer" means any polymers that are not found in nature, even if the polymers are made from naturally occurring biomaterials. Examples include, but are not limited to aliphatic polyesters, poly(amino acids), copoly(etheresters), polyalkylenes, oxalates, polyamids, tyrosine derived polycarbonates, poly(iminocarbonates), polyorthoesters, polyoxaesters, polyamidoesters, polyoxaesters containing amino groups, poly(anhydrides), polyphosphazenes and combinations thereof.

The term "biocompatible polymer" refers to any polymer which when in contact with the cells, tissues or body fluid of an organism does not induce adverse effects such as immunological reactions and/or rejections and the like.

The term "biodegradable polymer" refers to any polymer which can be degraded in the physiological environment such as by proteases. Examples of biodegradable polymers include, collagen, fibrin, hyaluronic acid, polylactic acid (PLA), polyglycolic acid (PGA), polycaprolactone (PCL), polydioxanone (PDO), trimethylene carbonate (TMC), polyethyleneglycol (PEG), alginate, chitosan or mixtures thereof.

In embodiments of the invention the polymer content of the fibre comprises over 85% glycolide, over 90% glycolide, over 95% glycolide, or consists of 100% glycolide.

Polyglycolic acid (PGA), also referred to as polyglycolide, is a biodegradable, thermoplastic polymer and the simplest linear, aliphatic polyester. It can be prepared starting from glycolic acid by means of polycondensation or ring-opening polymerisation of glycolide. PGA is characterised by hydrolytic instability owning to the presence of the ester linkage in its backbone and thus when it is exposed to physiological conditions, PGA is degraded by random hydrolysis. The degradation product, glycolic acid, is non-toxic and it can enter the tricarboxylic acid cycle after which it is excreted as water and carbon dioxide. The polymer has been shown to be completely resorbed by an organism in a time frame of four to six months.

In particular embodiments of the invention the glycolide is PGA.

In embodiments of the invention the fibre comprises a copolymer of a glycolide and/or a lactide and/or other suitable hydroxy acids. Examples of suitable copolymers include poly(lactic-co-glycolic) acid (PLGA), a co-polymer with lactic acid; poly(glycolide-co-caprolactone) (PGACL), a co-polymer with ε-caprolactone and poly(glycolide-co-trimethylene carbonate) (PGATMC), a co-polymer with trimethylene carbonate.

In embodiments of the invention the copolymer is poly(lactide-co-glycolide) (PLGA), wherein the ratio of PGA:PLA is about 85:15, or about 85.25:14.75, or about 85.50:14.50, or about 85.75:14.25; or about 90:10, or about 90.25:9.75; or about 90.50:9.50; or about 90.75:9.25; or about 91:9; or about 92:8; or about 93:7; or about 94:6; or about 95:5; or about 96:4; or about 97:3; or about 98:2; or about 99:1.

The invention further covers blends of PGA and a polyester. Examples of suitable blends include polyglycolic acid blended with polylactic acid (PGA/PLA) and also polydioxanone blended with polyglycolic acid (PDO/PGA). It is envisaged that the blends can consist of at least one copolymer.

All stereoisomeric forms of the polymers are envisaged.

Scaffolds or scaffolds according to the present invention have advantageously been found to be dimensionally stable when exposed to physiological conditions and as such upon implantation into the body they exhibit a minimal shrinkage of less than 10%, and more particularly less than 5% as illustrated in Table 1.

TABLE 1

Dimensional stability of polymer scaffolds

| Material | % shrinkage after 24 h at 37° C. in PBS |
| --- | --- |
| PDLA | 72 ± 2 |
| PLGA (75/25) | 74 ± 4 |
| PGA (0.29 and 2.19 μm fibres) | 4 ± 4 |
| PLGA (10/90) 0.9 μm fibre | 18 ± 3 |
| PLGA (10/90) 2.7 μm fibre | 10 ± 2 |
| PCL | 0 ± 0 |
| PDLA + 5% PGA | 73 ± 3 |
| PDLA + 10% PGA | 75 ± 3 |
| PDLA + 25% PGA | 34 ± 1 |
| PDLA + 50% PGA | 35 ± 3 |

TABLE 1-continued

Dimensional stability of polymer scaffolds

| Material | % shrinkage after 24 h at 37° C. in PBS |
|---|---|
| PDLA + 75% PGA | 48 ± 1 |
| PDLA + 25% PLLA | 36 + 4 |
| PDLA + 50% PLLA | 34 ± 3 |
| PDLA + 75% PLLA | 32 ± 1 |
| PLGA + 5% PGA | 53 ± 2 |
| PLGA + 10% PGA | 35 ± 3 |
| PLGA + 25% PGA | 47 ± 1 |
| PLGA + 50% PGA | 49 ± 4 |
| PLGA + 75% PGA | 55 ± 1 |
| PLGA + 25% PLLA | 41 ± 2 |
| PLGA + 50% PLLA | 43 ± 7 |
| PLGA + 75% PLLA | 37 ± 1 |
| PDLA + 5% PCL | 85 ± 1 |
| PDLA + 10% PCL | 85 ± 2 |
| PDLA + 20% PCL | 83 ± 0 | poly(D,L-lactic acid) = PDLA
poly(lactide-co-glycolide = PLGA
poly($\epsilon$-caprolactone) = PCL
polyglycolic acid = PGA
poly(L-lactide) = PLLA poly(D,L-lactic acid)=PDLA polyglycolic acid=PGA poly(lactide-co-glycolide=PLGA poly(L-lactide)=PLLA poly($\epsilon$-caprolactone)=PCL phosphate buffer saline solution=PBS This initial dimensional stability results in the surface area and pore size remaining relatively stable during the initial phases of cellular interaction with the scaffold. For example, this stable porosity is important in enabling cell migration towards the centre of the scaffold.

In embodiments of the invention the scaffold is a non-woven. Non-woven fabrics are those which are neither woven nor knit and which are typically manufactured by putting small fibres together to form a sheet or web, and then binding them either mechanically (as in the case of felt, by interlocking them with serrated needles such that the inter-fibre friction results in a stronger fabric), with an adhesive, or thermally (by applying binder (in the form of powder, paste, or polymer melt) and melting the binder onto the web by increasing temperature).

In further embodiments of the invention the scaffold is manufactured by electrospinning (either solution or melt electrospinning), phase separation, melt-blowing, spinning or self-assembly. Electrospinning is the preferred method of manufacture because it readily allows scale-up to industrial levels of production, particularly in terms of appropriately sized scaffolds for use in medical applications.

In order to increase the bioaffinity and recognition of the cells proliferating and/or migrating through the scaffold and/or to increase the therapeutic potential of the scaffold it is envisaged that at least one agent for promoting cell colonisation, differentiation, extravasation and/or migration is associated with a fibre of the scaffold. This at least one agent can be a biological, chemical or mineral agent, which can be attached to, embedded within or impregnated within the fibre.

An example of a suitable agent is an anti-microbial agent such as silver, iodine or chlorhexidine.

The agent can be provided within the polymer solution prior to fibre formation. Additionally or alternatively the at least one agent can be associated with the fibre post-formation.

There is also provided the use of the scaffold for a drug delivery application. A medicinal compound may be associated with the fibres of the scaffold.

According to a further aspect of the invention there is provided a medical dressing, for example a wound dressing comprising a scaffold according to the invention.

Burns that cover large surface areas of the body require specialised therapies that restore an epidermis like function as soon as possible after injury. The primary purpose of these dressings is restore the body's ability to retain water and resist environmental insult. This can be achieved by covering the wound using an occlusive dressing often referred to as a synthetic epidermis which is provided by a silicone sheet, acting as an epidermal analogue, in a number of commercially available products. However healing rates beneath these occlusive dressings remain sub-optimal and may be improved dramatically by the incorporation of an additional layer that cells respond to appropriately.

Biobrane® (Dow Hickam Pharmaceuticals Inc) developed in 1979 by Woodroof, consists of a custom-knitted nylon fabric mechanically bonded to an ultrathin silicone membrane. The entire dressing is uniformly coated with porcine type I collagen peptides, covalently and independently bonded to the dressing and acting as the dermal analog.

Transcyte® (Smith & Nephew, Plc) consists of a polymer membrane and newborn human fibroblast cells cultured under aseptic conditions in vitro on a nylon mesh.

Both Biobrane® and Transcyte® are applied to burn wounds with the nylon mesh side against the wound bed and the silicone layer uppermost. The primary mode of action is that the silicone layer acts as a synthetic epidermis and prevents excessive water loss from the patient through the compromised epidermis and also prevents environmental insult to the injury. A secondary mode of action is that the proteins present underneath the silicone layer exert a biological effect and encourage the re-epithelialisation of the surface of the burn, resulting in faster closure.

There are concerns over the use of natural polymers in these synthetic burns dressings because of the potential for pathogen transmission and immune reactions.

The scaffold of the present invention when deposited, for example by electrospinning, onto an appropriate substrate has been identified as providing an ideal burns dressing overcoming the problems associated with the biologically derived materials present within the prior art dressings.

In embodiments of the invention the substrate layer is composed of biological, synthetic or blended materials. Suitable materials include polymers, for example: polycellulose, polyurethane, polystyrene, polyimides, polyamides, resins, nylon, silicone, polyester, polyolefin for example polyethylene, polypropylene, polybutylene, copolymers and mixtures thereof.

Silicone substrates can be classified according to their permeability to vapour and air. Occlusive silicone substrates are impermeable to vapour and air. Perforated silicone substrates allow vapour and air exchange through the perforations whilst permeable silicone substrates are vapour and air transmissible.

In specific embodiments of the invention the silicone substrate is a silicone-based film, for example Cica-Care® (T J Smith & Nephew Limited).

The substrate layer may be removably attached to the scaffold using a suitable adhesive. Alternatively the scaffold may be electrospun directly onto the substrate layer. This provides a relatively low cost means to manufacture the dressing.

In such a dressing, the substrate layer will prevent excessive water loss and environmental insult to the burn wound. The fibrous scaffold will encourage epithelial cell migration and proliferation and so will encourage re-epithelialisation and wound closure. When re-epithelialisation is complete the semi-permeable barrier layer, is peeled away from the scaffold, with the resorbable fibres remaining in the wound bed degrading over time into harmless breakdown products.

It is further envisaged that layers of scaffold having different architectures can be deposited, for example by electrospinning, onto a substrate, such as a silicone-based film. For example, the layers closest to the silicone-based film may consist of fibres having a small diameter and pores size in order to encourage keratinocyte migration over the surface of the fibres, beneath the silicone-based film. The layers of the scaffold which are located, in use, deeper within the wound bed may consist of fibres having a larger diameter and pore size in order to allow the infiltration of other cell types such as fibroblasts and endothelial cells.

It is also envisaged that the active agents may be associated with the scaffold, for example, agents that improve scar resolution and prevent scar formation, for example: insulin, vitamin B, hyaluronic acid, mitomycin C, growth factors (TGFβ), cytokines, corticosteroids and/or agents that promote re-epithelialisation.

According to a further aspect of the invention there is provided a medical dressing, for example a burns dressing comprising a scaffold deposited onto a substrate, such as a silicone-based film.

According to a still further aspect of the invention there is provided a method of manufacturing a scaffold comprising electrospinning fibres which comprise a glycolide onto a target and wherein the mean fibre diameter is between from about 1.2 to 4.0 microns.

In embodiments of the invention the glycolide is PGA.

The manufacture of the scaffold can be performed within a laboratory or a manufacturing plant. The scaffold can be spun onto an appropriate target, packaged and sterilised. Alternatively the method can be performed in situ, for example, at the site of the wound, such that the electrospun scaffold is directly spun into the wound bed. This can be achieved by the use of a hand-held electrospinning device. A top layer, such as a silicone-based film can then be applied to the upper surface of the scaffold.

In embodiments of the invention the scaffold forms a part of a burns dressing, with the fibres being electrospun onto one side of a semi-permeable barrier layer, such as a silicone-based film. When the burn has healed the semi-permeable barrier layer is peeled away from the remaining scaffold, with the scaffold having been bioresorbed within the wound.

According to a further aspect of the invention there is provided a method of promoting tissue regeneration in a wound, the method comprising the step of applying a wound dressing to the wound, the dressing comprising a scaffold including fibres comprising polyglycolic acid, wherein the mean fibre diameter is between from about 1.2 to 4.0 microns.

There is also provided use of a medical dressing comprising the scaffold of the present invention deposited onto a semi-permeable barrier layer for treating a dermal condition of an animal, including both humans and non-human animals. The dermal condition may be a burn on an animal's skin. The medical dressing may be used to treat a burn that extends to at least the epidermis of the animal's skin. The medical dressing may also be used to treat a burn that extends to the dermis or the subcutaneous fat region of an animal's skin.

There is a need for devices and methods which enable rapid seeding of cells onto scaffolds suitable for repairing tissue defects. This is particularly important for autologous procedures, where the patient's own cells are being used and it is desirable to harvest cells, seed the cells onto a scaffold and implant the cell-seeded scaffold into a tissue defect in one medical procedure. Advantageously the time between harvesting the tissue and implanting the seeded device should be 30 minutes or less. Advantageously the procedure should be a single step procedure.

Thus, according to a further aspect of the invention there is provided the use of the scaffold according to the present invention for the selective capture of a population of cells from a cell source material.

The scaffold can be described as being "seeded" with the captured cells. In embodiments of the invention the scaffold is advantageously seeded with nucleated cells, for example platelets and/or leukocytes.

Platelets and leukocytes play key roles in wound healing.

Platelets or thrombocytes are the cell fragments circulating in the blood that are involved in the cellular mechanisms of primary hemostasis leading to the formation of blood clots.

White blood cells or leukocytes are cells of the immune system which defend the body against both infectious disease and foreign materials. The platelets at the wound site release growth factors such as platelet-derived growth factor which attracts white blood cells and stimulates the release of other chemical mediators (such as cytokines) necessary for wound healing. The inflammatory phase is a key stimulant to the subsequent phases of the healing process and may be prolonged in an infected, chronic or necrotic wound leading to chronic inflammation. Monocytes, a subset of white blood cells differentiate into macrophages which secrete growth factors that attract and activate local cells, such as endothelial cells and fibroblasts, to initiate granulation tissue formation. Prolonged inflammation results in proliferation in macrophage activity leading to an increase in the release of cytokines, which further stimulate the inflammatory process.

In embodiments of the invention the scaffold comprises electrospun fibers, typically having a fibre diameter of from about 50 nanometers to 5 microns, particularly of from about 1.2 to 4.0 microns, more particularly of from about 1.5 to 3.5 microns and more particularly still of from about 1.9 to 2.6 microns.

In embodiments of the invention the scaffold has a pore size of 1 to 25 microns, and more preferably between 8 and 12 microns.

The cell source material is derivable from, for example, bone marrow, blood (such as umbilical cord blood or peripheral blood), plasma, serum, urine, amniotic fluid, seminal fluid, cerebrospinal-fluid, lymph or saliva. The cell source material can be introduced into the device undiluted. Alternatively it can be diluted or made into a suspension using phosphate buffered saline, tissue culture media or other diluents known in the art. Alternatively, isolated cells can be used as a cell source material. Suitable cells include stem cells, progenitor cells, bone cells, chondrocytes or fibroblasts, but can be any cell that can be isolated and is appropriate for the tissue defect to be repaired. The cells will typically be a suspension in a suitable diluent, as hereinbefore mentioned.

The cell source material can be filtered through a pre-filter before it enters the scaffold. This pre-filtering step can take place prior to the cell source material being introduced into the device. Alternatively the cell source material can pass through a pre-filter which is provided within the device, at any point prior to entry into the scaffold. The pre-filter can be a coarse filter (approx. 70 micrometer filter).

In embodiments of the invention the scaffold is provided in a cell capturing device wherein the scaffold is arranged in the device enable the cell source material to be filtered more readily through the scaffold.

Filtration of the cell source material through the scaffold can be either via passive or forced filtration. Forced filtration is particularly advantageous as this increases the speed at which the cell source material is filtered, which is particularly beneficial if the device is being used in the operating room to derive autologous cells from the patient's own body fluid, where minimising the time that the patient is on the operating table is crucial. Additionally forced filtration results in the captured cells being distributed substantially throughout the scaffold.

A pressure generating device can provide either negative or positive pressure to the device to enable this forced filtration.

A suitable negative pressure generating device is a vacuum pump. The pump can be used to deliver a vacuum of at least 5 mb below atmospheric pressure to the device. In embodiments of the invention the vacuum pump can deliver a vacuum of up to 900 mb below atmospheric pressure if required. The vacuum can be applied either before, during or after the cell source material is introduced into the pre-filtration chamber.

Alternatively, a positive pressure generating device is used to apply positive pressure to force the cell-containing fluid through the scaffold. This positive pressure may replace or supplement the negative pressure source. A suitable positive pressure generating device is a syringe.

The forces to which the scaffold is exposed to during the application of positive or negative pressure to the device can be potentially damaging to the structure of the scaffold. The scaffold is therefore advantageously supported by a support structure. This structure allows the passage of cell source material whilst supporting the scaffold against the pressure. Suitable support structures include Hollander meshes, polyester, or nylon supports.

In use the cell source material is introduced into the pre-filtration chamber within the cell capturing device and a positive or negative pressure is applied to draw the cell source material through the scaffold. A first population of cells contained within the material is captured by the scaffold whilst a second population of cells passes through the scaffold into the post-filtration chamber.

In embodiments of the invention the first population of cells comprises or consists of platelets and/or leukocytes.

In embodiments if the invention the second population of cells comprises or consists of erythrocytes. This second population may in some circumstances be considered to be "waste" and is immediately disposed of. Alternatively this second population may optionally be returned to the pre-filtration chamber for at least a second filtration cycle.

In embodiments of the invention the scaffold including the captured cell population is directly implanted into a site. In such embodiments the scaffold is preferably biocompatible and bioresorbable. Such a scaffold consists of a population of cells, such as platelets and/or leukocytes, which are therapeutically beneficial at the time of implantation. Additionally the scaffold has an optimal architecture to promote endogenous cell adhesion, proliferation and migration whilst also demonstrating dimensional stability over the time required for these initial cellular processes.

The scaffold may be implanted into any site within the human or animal body (that is a non-human animal), in which the scaffold would be therapeutically beneficial. For example, the scaffold may be implanted into a soft tissue defect. The term soft tissue refers to tissues that connect, support, or surround other structures and organs of the body. Soft tissue includes muscles, tendons, fibrous tissues, fat, blood vessels, nerves, and synovial tissues and skin.

In other embodiments of the invention the captured cell population is washed out of the scaffold and used as an isolated cell source.

The cell capture device is preferably disposable, although it may be manufactured of materials suitable for sterilization. Such sterilization methods may include autoclaving, e-beam, ethylene oxide or other methods known in the art.

According to the present invention there is provided a method for rapidly seeding cells onto a scaffold including the steps of applying a cell source material to a scaffold and applying either a negative or a positive pressure such that the cell source material is distributed substantially throughout the scaffold.

According to the present invention there is provided a method for removing erythrocytes from a heterogeneous cell source material. This method is based on the fact that red blood cells differ largely in size from the other components in this heterogeneous cell source, in that they are substantially smaller. So a large proportion of the red blood cells under at least 5 mb of vacuum find their way through the pores in the scaffold and pass out the other side, whereas the other larger components remain trapped and can not pass through the scaffold pores.

According to the present invention there is also provided a kit of parts comprising pressure generating means, a delivery chamber, a scaffold chamber, a scaffold support structure and a receiving chamber. The kit is optionally supplied with coarse filtering means, for example a 70 micrometer filter. The kit is optionally supplied with a cell source material.

DEFINITIONS

Unless otherwise specified the term "comprising" and "comprise" and grammatical variants thereof, are intended to represent "open" or "inclusive" language such that they include recited elements but also permit inclusion of additional, unrecited elements.

As used herein, the term "about", in the context of concentrations of components of the polymer fibre, typically means +/−5% of the stated value, more typically +/−4% of the stated value, more typically +/−3% of the stated value, more typically +/−2% of the stated value, more typically +/−1% of the stated value and even more typically +/−0.5% of the stated value.

Exemplary, non-limiting embodiments of a scaffold, method of preparing the scaffold and use of the scaffold will now be disclosed.

Method for Making PGA Scaffolds with Appropriate Fibre Diameter Using Electrospinning 1.729 g PGA with an inherent viscosity of 1.24 dL/g, supplied by Lakeshore Biomaterials, was dissolved in 18.200 g hexafluoroisopropanol (HFIP) supplied by Apollo Scientific, to form a 9.5% w/w PGA solution. This polymer solution was filtered through a 10 μm pore, 50 mm diameter Whatman disk filter into a 10 ml syringe residing in a syringe pump set to dispense at 0.03 ml/minute. The syringe exit was attached to a flexible plastic tube (1.5 mm internal diameter) with its other end attached to an 18-gauge needle that had been horizontally cut to remove its taper. The needle was clamped vertically, 15 cm above a target within a box (internal dimensions: 55 cm wide×60 high×60 deep, used to minimise air movement during electrospinning. The target consisted of an aluminium mandrel (5 cm diameter×10 cm long) attached to a motor to enable the target to be rotated at 50 rpm so that an even coating of fibrous material was produced. The target was covered in replaceable baking paper (12.7×17.5 cm) to aid separation of the fibrous scaffold from the target.

To initiate the electrospinning process, a voltage was applied to the needle via a Glassman voltage generator while the target was earthed. The electrospinning process was initiated when sufficient voltage was applied to cause the polymer solution droplets to stop dripping off the needle tip and instead become drawn away as a polymer jet. The polymer jet split up into many tiny jets, which were accelerated towards the earthed rotating target, where they were deposited as fibres. The minimum voltage required to initiate the electrospinning process and to maintain a stable droplet at the needle tip was used. The run time was adjusted according to the scaffold depth required.

The electrospun scaffolds were vacuum dried at room temperature for at least 3 days to minimise residual HFIP solvent.

Determination of Fibre Diameter

Figure 1:
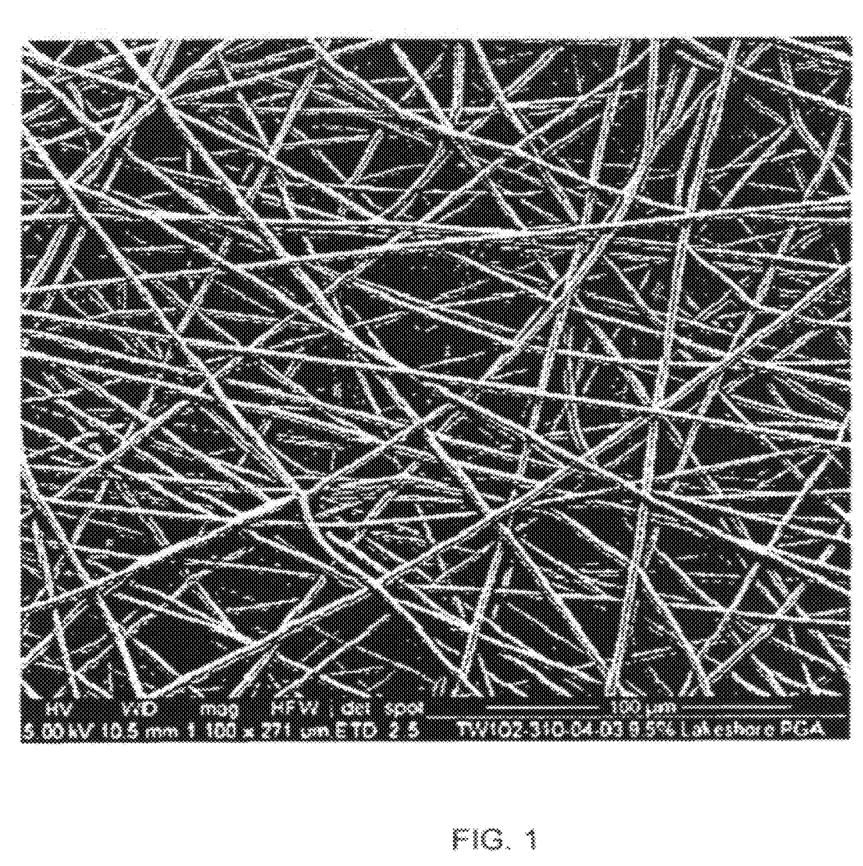
FIG. 1 illustrates a scanning electron micrograph of a scaffold according to the invention.

Scanning electron micrographs (SEM's) as illustrated in FIG. 1 were obtained for the scaffolds by cutting out 10 mm scaffold circles, adhering them to 10 mm metal stubs and sputter coating the cut scaffolds under vacuum with a gold/palladium alloy to reduce surface charging. The coated scaffolds were imaged using a scanning electron microscope (JSM-6400) set to an accelerating voltage of 5 kV, Tungsten filament current of 210 µA and a working distance of 15 mm.

Fibre diameters were determined manually from the SEM images by randomly measuring the fibre diameters of a sample of 20 fibres in one SEM image with a ruler, converting to actual fibre diameters using the scale bar and calculating the mean and standard deviation.

Results

The mean fibre diameter was determined to be 2.42±0.35 µm.

Dimensional Stability Test

Square samples ($3\times3$ cm$^2$) were cut out of the scaffolds using scissors. The samples were then placed in polystyrene Petri Dishes, covered with 15 mL Phosphate Buffer Saline solution (PBS), and placed in an incubator at 37° C. for 24 hours. After rinsing the wet samples in deionised water, all were measured again and their dimensions compared with the initial ones by expressing a "% shrinkage" defined as: % shrinkage=100×(initial area−final area)/initial area. Each type of scaffold was tested in 3 replicates. Results are shown in Table 1.

Biological Response

Biological efficacy of a range of electrospun scaffolds with a range of architectures was assessed using 3 independent cell based assays. Assays to measure cell adhesion, proliferation and migration into the scaffold were carried out.

Adhesion Assay:

Electrospun scaffolds were prepared from a range of PGA solution concentrations resulting in a range of scaffold architectures ranging from approximately 200 nm to approximately 3 µm. A PGA felt (control sample) with fibres of approximately 20 vm in diameter was assessed in parallel. The scaffolds/controls were cut in to 13 mm diameter discs using the clickerpress (Samco SB-25), placed into Minucell clips (Minutissue Vertriebs, GmbH) and sterilised under U.V. light for 20 mins using a Uvasol 400. Human dermal fibroblasts were used throughout at passage 13 and lower and were confirmed to be free from Mycoplasma infection by DAPI staining (Vector Labs)

Human dermal fibroblasts were seeded onto the samples and controls in 100 µl of DMEM+10% FCS (Sigma) at a density of 100,000 cells per scaffold and incubated for one hour at 37° C., 5% $CO_2$. A standard curve was also set up by seeding fibroblast cells directly into tissue culture wells, maximum density of $1\times10^5$, minimum of $0.3\times10^4$ cells per well (total volume of 400 µL). After the incubation period, all scaffolds were dipped in sterile PBS to remove unattached cells and transferred to a new 24-well plate. 400 µL DMEM+ 10% FCS was added to each scaffold and 40 µL WST-1 (Roche diagnostics) added to all wells (including to those of the standard curve). The plates were incubated for an additional hour at +37° C., +5% $CO_2$. 100 µL media from each well was then transferred (in triplicate) to a 96-well plate. Optical absorbance at 450 nm (ref. 655 nm) was proportional to the number of viable cells present on each sample and was read using the Multiskan Ascent platereader. The absorbance value was converted to cell number using the standard curve and results expressed using these values.

Experiments were performed in triplicate in three independent experiments.

Proliferation Assay:

Electrospun scaffolds were prepared from a range of PGA solution concentrations resulting in a range of scaffold architectures ranging from approximately 200 nm to approximately 3 µm. A PGA felt (control sample) with fibres of approximately 20 µm in diameter was assessed in parallel. The scaffolds/controls were cut in to 13 mm diameter discs using a clickerpress (Samco SB-25), placed into Minucell clips (Minutissue Vertriebs, GmbH) and sterilised under U.V. light for 20 mins using a Uvasol 400. Human dermal fibroblasts were used throughout at passage 13 and lower and were confirmed to be free from Mycoplasma infection by DAPI staining (Vector Labs).

Human dermal fibroblasts were seeded onto the samples and controls in 100 µL of DMEM+10% FCS (Sigma) at a density of 40,000 cells per scaffold and allowed to adhere for one hour at 37° C., 5% $CO_2$. Samples were incubated under culture conditions for either 1hour (to provide a baseline attachment measurement) or for 48 hours (to measure cellular proliferation over time). At each time point, a standard curve was set up by seeding fibroblast cells directly into tissue culture wells, maximum density of $1\times10^5$, minimum of $0.3\times10^4$ cells per well and allowed to attach for 1 hour prior to cell measurement. Following a 1 hour period in which the cells attached to the scaffolds, all scaffolds were dipped in sterile PBS to remove unattached cells and transferred to a new 24-well plate. Samples used to measure the 1hour (baseline) measurement were then transferred into 400 µL DMEM+ 10% FCS +40 µL WST-1(Roche diagnostics). The plates were then incubated for an additional hour at 37° C., 5% $CO_2$. Samples used to measure the 48 hour timepoints were dipped in PBS and transferred to new 24-well plates in 400 µL DMEM+10% FCS and the plates incubated for an additional 48 hours. After 48 hours, a fresh cell standard curve was prepared as above and the number of cells measured using WST as above. After incubation with WST-1, 100 µL media from each well was transferred (in triplicate) to a 96-well plate. Optical absorbance at 450nm (ref. 655nm) was proportional to the number of viable cells present on each sample and was read using the Multiskan Ascent platereader. The absorbance value was converted to cell number using the standard curve and results expressed using these values. Experiments were performed in triplicate in three independent experiments.

Migration Assay:

An assay was developed to assess the ability of cells to migrate into and through test sample scaffolds. The experimental set up is illustrated in the FIG. 2.

Figure 2:
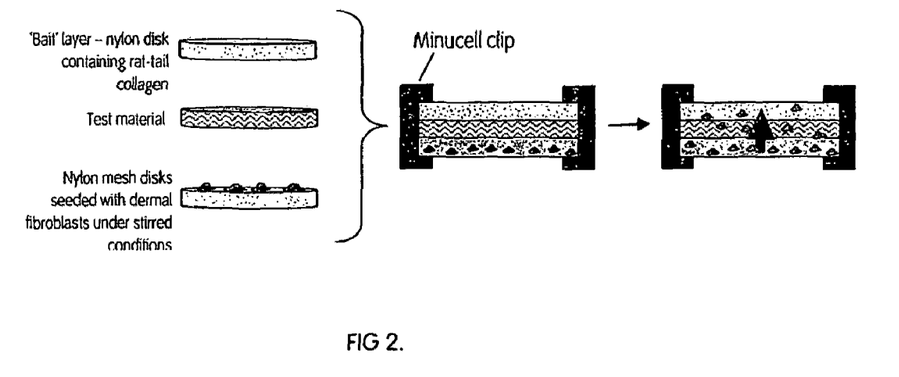
FIG. 2 illustrates a schematic of the cell migration assay used to measure cell migration through a scaffold according to the invention.

Cell seeded nylon discs comprise the bottom layer of the sandwich as shown in FIG. 2.

Human Dermal Fibroblast (HDF) cells were seeded onto 13mm diameter nylon discs. Briefly, 7-12 million cells were added to a siliconised Techne flask containing 25 nylon discs and 50mL DMEM+10% FCS (TCM), then stirred at 45 rpm for 5 minutes every 15 minutes for 24 hours (in 5% $CO_2$ at 37° C.). The nylon discs were transferred individually into the wells of non-tissue culture plastic 24 well plates, each containing 2 mL TCM, and incubated in 5% $CO_2$ at 37° C. for an additional 3 days until cell confluence was reached.

Test samples comprise the middle layer of the sandwich as shown in FIG. 2.

Electrospun scaffolds were prepared from a range of polyglycolic acid (PGA) solution concentrations resulting in a range of scaffold architectures ranging from approximately 200 nm to approximately 3 µm. A PGA felt (control sample) with fibres of approximately 20 µm in diameter was assessed in parallel. The scaffolds/controls were cut in to 13 mm diameter discs using a clickerpress (Samco SB-25) and sterilised under U.V. light for 20 mins using a Uvasol 400.

The bait layer comprises the top layer of the sandwich as shown in FIG. 2.

Sterile nylon discs (13 mm diameter) were aseptically coated with rat tail collagen and allowed to air dry. The collagen coated nylon discs were used as the top layer as shown in FIG. 2.

Assay Protocol:

The three layers described above were clipped together in 13 mm Minucell clips (13 mm Minusheet, ref 1300, Minucell and Minutissue Vertriebs, GmbH). The minucell assemblies were transferred to the wells of non-tissue culture plastic 24 well plates each containing 2 mL DMEM/10% FCS (Sigma). The plates were incubated for 2 days at 37° C./5% $CO_2$. After this time the minucell assemblies were dismantled, the layers separated and transferred into individual wells of a 24-well plates containing 400 µL DMEM/10% FCS. 40 µL WST-1 reagent (Roche diagnostics,) was added to each well and the plates incubated for 1 hour at 37° C. in 5% $CO_2$. Triplicate 100 µL volumes were transferred to 96 well plates, and the absorbance read at 450 nm with reference at 655 nm on the Multiskan Ascent plate reader. A standard calibration curve of absorbance against cell number was prepared alongside the test plates for each assay carried out, and used to estimate the cell number present on each layer of the sandwich. The total cell number was calculated for each sandwich (sum of cell numbers for all three layers) and the cells present on the middle and top layers were estimated as a percentage of total cell number.

Figure 3:
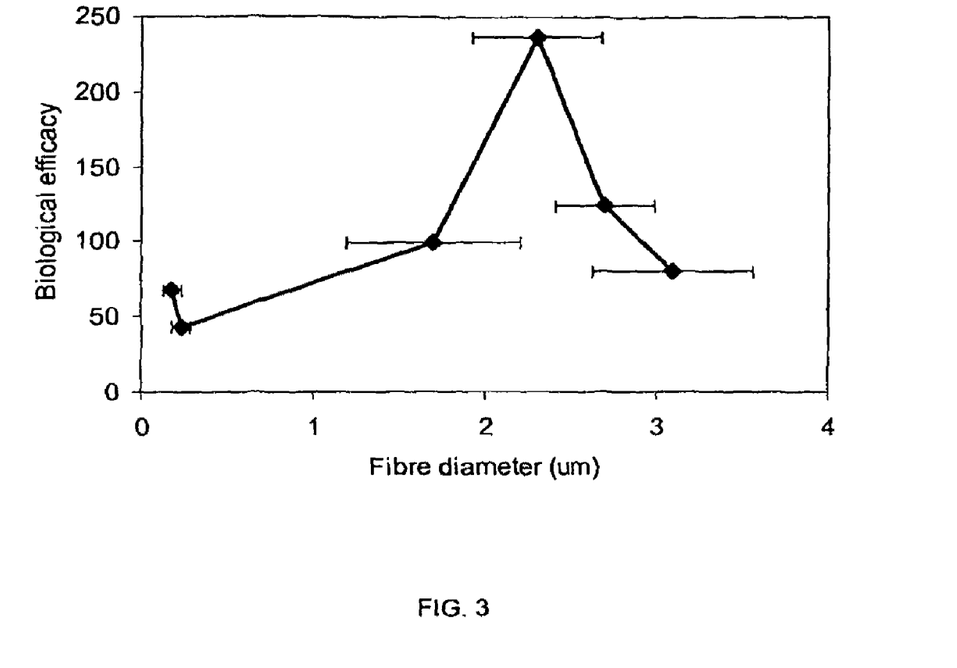
FIG. 3 is a graph illustrating the biological response of cells on a scaffold according to the invention.

Experiments were performed in triplicate in three independent experiments. In order to express the data as an overall biological response, the data from each assay were converted to a percentage change from a common control, in this case PGA felt. The biological response to the felt is expressed as 0. Combined results are shown in FIG. 3. This graph shows a clear peak of efficacy at approximately 2.5 µm fibres. This graph also shows the range of fibre diameters (x-axis error bars) obtained with each batch of scaffold of which the point on the graph is the mean.

Cell Capturing Device

Figure 4:
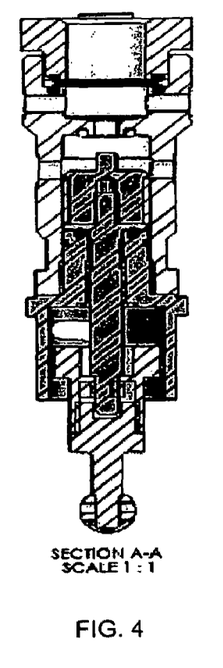
FIG. 4 shows an example of a cell capturing device comprising the scaffold of the invention.

Referring to FIG. 4, a delivery chamber 20 is in communication with scaffold chamber 40, which is in communication with a receiving chamber 70. Coarse filter 30 is positioned within delivery chamber 20. Scaffold support structure 50 is positioned within scaffold chamber 30. Scaffold 60 is situated on top of scaffold support structure 50. Vacuum pump 80 is operably connected to receiving chamber 70. Cell source material 10 is introduced to delivery chamber 20 and is drawn by the vacuum through course filter 30 into scaffold chamber 40, thence through scaffold 60 where a proportion of cell source material is retained and a proportion passes into receiving chamber 70.

EXAMPLE 1

Method of Manufacturing an Electrospun Scaffold for Use in the Cell Capturing Device Electrospun scaffolds were produced by the process of electrospinning using polyglycolide (PGA), poly(lactide-co-glycolide) (PLGA), polyglycolide trimethyl carbonate (PGA-co-TMC), polycaprolactone (PCL), poly(D-lactide) (PDLA) and poly(L-lactide) (PLLA). The polymer solution was placed into a 10 ml syringe residing in a syringe pump, which was set to dispense the polymer at the required rate. The syringe tip was then attached to a tube (1.5 mm internal diameter) with other end attached to an 18 gauge needle that had been horizontally cut to remove its taper. The needle was clamped vertically between 10 and 20 cm above a target within a box (internal dimensions: 55 cm wide×60 high×60 deep) used to minimise air movement while electrospinning. The target consisted of a metal roller, known as the mandrel, which was attached to a motor that was rotated up to 2000 rpm to give an even coating of nano-fibrous material. The mandrel was covered in replaceable baking paper to aid separation of the scaffold from the metal surface. To initiate the electrospinning process, a voltage was applied to the needle while the target was grounded. At a sufficient voltage, polymer solution stopped dripping off the needle tip and was instead drawn away as tiny polymer jets towards the grounded rotating target where they were deposited as nano-fibers.

Scaffold fibre diameters were determined as follows— Normal: 2.41±0.25 µm; 2.41±0.22 µm; Extra thick: 2.43±0.60 µm; 2.40±0.19 µm.

EXAMPLE 2

Isolation of Bone Marrow Cell Suspension

Trabecular bone was removed from two femoral heads from freshly culled pigs obtained from the abattoir on the day of sampling. The femur was detached from the knee and all the muscle, cartilage, tendons and any other tissue that could contaminate the marrow sample were removed. The femoral head was dissected using a coping saw to expose the trabecular bone, which was removed with a borer under sterile conditions.

EXAMPLE 3

Cell Suspension Dilution and Optimum Concentration

The cells isolated from bone marrow from the femoral head were initially a solid fraction, which would not pass through the meshes, so the cells were diluted into to a fluid fraction. The bone marrow was diluted down in either phosphate buffer saline (PBS), plasma or fresh porcine blood to a concentration of $1\times10^7$ white blood cells (WBC)/ml. A 100 µl aliquot of the cell suspension was removed for counting on the Coulter counter (Beckman Coulter Ac.T 5 diff. Counter). The Beckman Coulter counter counted the number of categories of both white and red blood cells contained within the sample based on both size and granularity, enabling measurements to be taken of the initial and final cell concentrations of the various cells, thus allowing the percentage of mononuclear cells captured on the scaffold to be calculated.

EXAMPLE 4

Different Cell Types were Investigated

The cell-seeding device has been used with a variety of different cell source material, including human bone marrow, porcine bone marrow, porcine bone marrow stromal cells and also dermal fibroblasts. Human bone marrow was obtained directly as a bone marrow aspirate from a human donor. Porcine bone marrow stromal cells and human dermal fibroblasts were taken from tissue culture expanded sources. These cell sources were obtained as a fluid and diluted down as the solid bone marrow fraction as described in Example 3. Results were comparable and repeatable between differing cell source materials, with similar mononuclear fractions being captured on the electrospun scaffold.

EXAMPLE 5

Method of Seeding Cells onto the Electrospun Scaffold 5 mls of the said cell suspension was added into the delivery chamber at the top of the cell-seeding device, under vacuum. In this chamber there was an initial 70 micron filter to trap any large particles, e.g. bone chips. The majority of the fluid passed straight through down into the scaffold chamber containing the electrospun scaffold supported on a stainless steel Hollander mesh. The majority of the larger mononuclear cell fraction was captured on or within the electrospun scaffold, with the smaller fraction being drawn through the mesh into the receiving chamber. The scaffold seeded with cells was removed and the waste cells in the receiving chambered disposed of.

Electrospun scaffolds (with a pore size of 12+/−4 μm) captured over 90% of nucleated cells and removed a high percentage of red blood cells.

| | % Nucleated cells retained in scaffold | % Erythrocytes removed form cell source material | % Platelets removed from cell source material |
|---|---|---|---|
| Experiment 1 | 94.8 +/− 2.76 | 87.5 | 100 |
| Experiment 2 | 92.8 +/− 2.64 | 57.6 | 100 |
| Experiment 3 | 93.7 +/− 2.23 | 79.6 | 100 |

EXAMPLE 6

Investigation of Pore Size

Electrospun scaffolds were most effective with pores sizes of between 7-15 μm at selectively capturing nucleated cells.

| | % Nucleated cells retained in scaffold | % Non-nucleated removed form cell source material |
|---|---|---|
| 7-15 μm | 98.9 +/− 2.4 | 60 +/− 14.1 |
| 15-20 μm | 84.9 +/− 4 | 98.8 +/− 5.3 |

EXAMPLE 7

Investigation into Scaffold Material Type

Both PGA and PLGA electrospun fibres yielded identical results.

| | % Nucleated cells retained in scaffold | % Non-nucleated removed form cell source material |
|---|---|---|
| PGA | 93 +/− 10 | 72.6 +/− 15.1 |
| PLGA | 98.9 +/− 2.4 | 60 +/− 14.1 |

EXAMPLE 8

Comparison Between Electrospun Scaffolds and Non-Woven Meshes

Electrospun scaffolds were also compared to other non-woven meshes in combination with a support mesh yield and data shows that these electrospun scaffolds yield better results, especially in relation to capturing the mononuclear cell population.

| | % Nucleated cells retained in scaffold | % Non-nucleated removed form cell source material |
|---|---|---|
| Electrospun scaffold | 96.4 +/− 2.6 | 66.3 +/− 14.6 |
| Non-woven polyester scaffold | 61.5 +/− 11.4 | 98 +/− 4.1 |

EXAMPLE 9

Blood Cell Capture on Electrospun Scaffolds

PGA scaffolds, 100 μm=normal and 300 μm=extra thick in depth.

| | Material & Solution concentration | Feed rate (ml/min) | Voltage (kV) | Accumulation time (min) |
|---|---|---|---|---|
| Normal | PGA, 8.5% | 0.03 | 7.5 | 60 |
| Extra thick | PGA, 8.5% | 0.03 | 7.5 | 180 |

Method

Approximately 17 ml fresh human blood was collected by venepuncture into two ACD-A vacutainers, with informed consent from volunteers. Alternatively, porcine blood was collected in bottles containing 4% (w/v) sodium citrate tribasic solution at a ratio of 1:9 (sodium citrate to blood). White blood cell, platelet and red blood cell counts were measured using the Coulter® A$^c$•T™ 5diff counter.

The device was connected to a vacuum pump (ILMVAC) set at 100 mBar below atmospheric pressure. A 30 mm PGA electrospun scaffold was clamped in place, supported by a 250 μm metal mesh, also 30 mm diameter. Electrospun PGA scaffolds were sterilised by exposure to UV light for 20 mins. Prior to filtering blood, each scaffold was pre-wetted by filtering 5 ml sterile PBS.

Three replicates of 5 ml blood, from three human or porcine donors were filtered through pre-wetted scaffolds. The filtrates were counted using the Coulter counter and compared to original blood cell counts to determine capture rates for each cell type.

Figure 5:
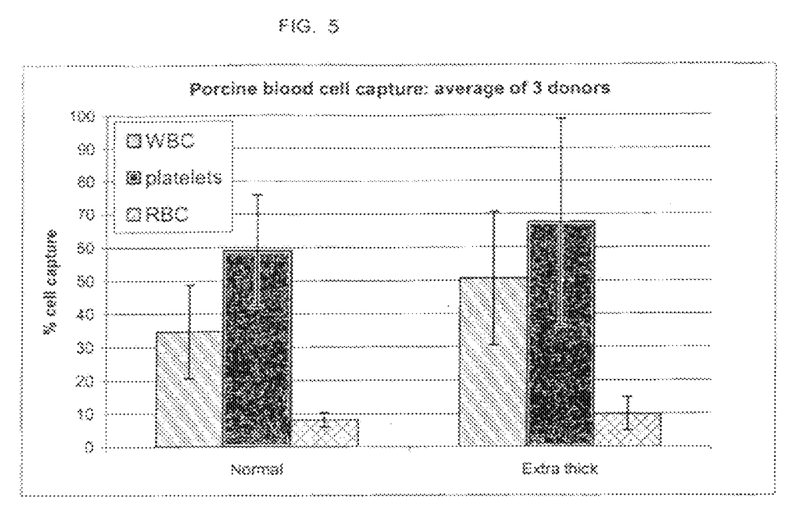
FIG. 5 illustrates rates of cell capture from porcine blood samples on an electrospun scaffold according to the invention.
Figure 6:
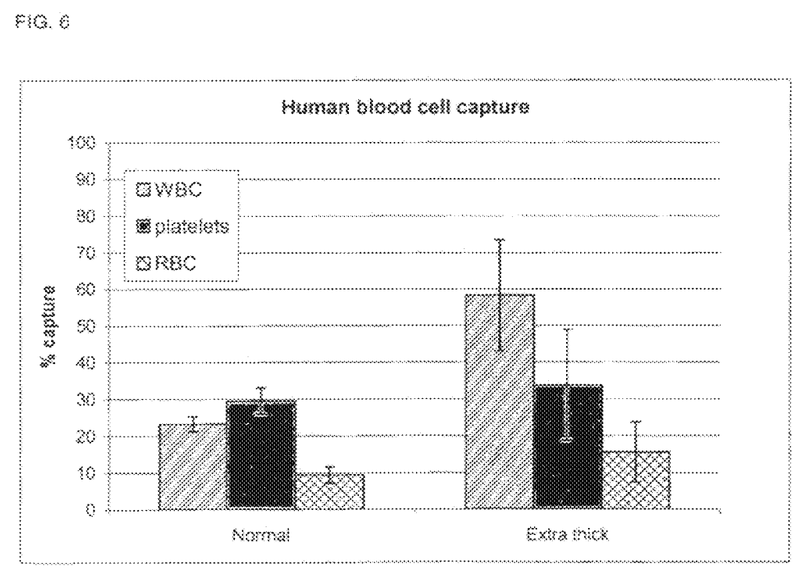
FIG. 6 illustrates rates of cell capture from human blood samples on an electrospun scaffold according to the invention.

Results are shown in FIG. 5 and 6.

EXAMPLE 10

Effect of Different Pre-Wetting the Scaffold with Various Solutions on Blood Cell Capture Rates Method PGA scaffolds, 100 μm (normal) and 300 μm (extra thick) in depth, were prepared by electrospinning and cut into 30 mm discs as described above. Three replicates of 5 ml porcine blood, containing 4% (w/v) sodium citrate tribasic solution at a ratio of 1:9 (sodium citrate to blood), from three different donors were filtered through the scaffolds supported by a 250 μm metal mesh and pre-wetted by filtering either 5 ml water, 5 ml PBS, 5 ml DMEM+10% FCS or left dry, using the device and a vacuum 100 mBar below atmospheric pressure. White blood cell, red blood cell and platelet counts in the filtrate were measured using the Coulter® A$^c$•T™ 5 diff counter, and compared to cell counts in the original blood samples.

Figure 7:
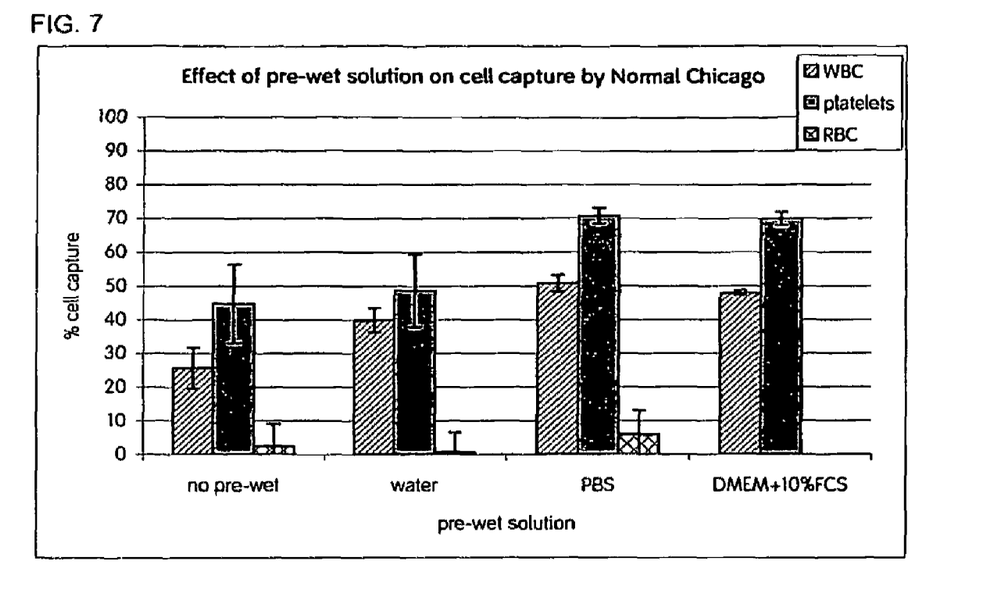
FIG. 7 shows the effect of pre-wetting a 100 μm thick PGA electrospun scaffold with various solutions, on the rates of cell capture from human blood samples.
Figure 8:
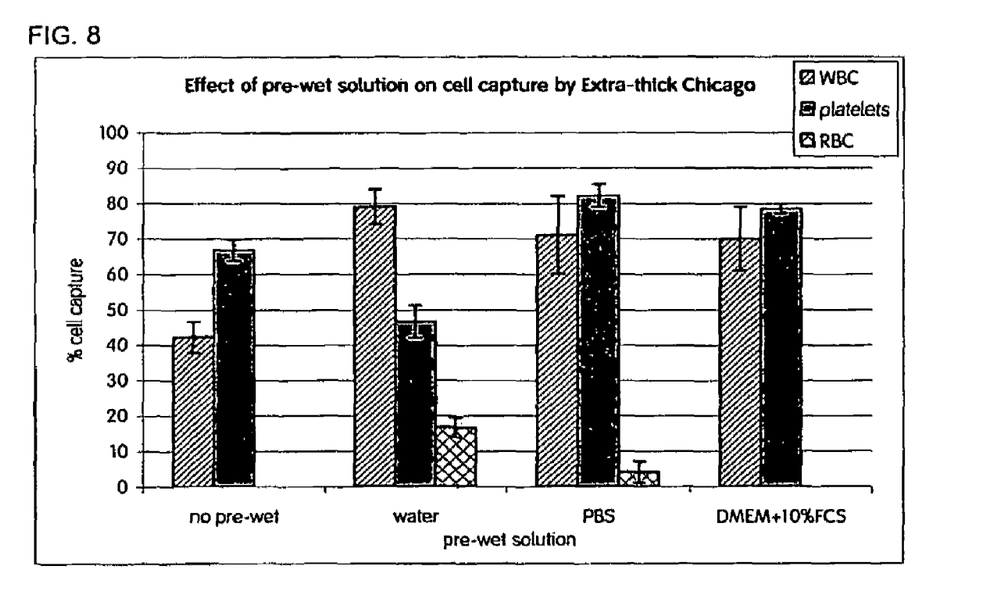
FIG. 8 shows the effect of pre-wetting a 300 μm thick PGA electrospun scaffold with various solutions, on the rates of cell capture from human blood samples.

Results are shown in FIGS. 7 and 8

The invention claimed is:

1. A scaffold comprising fibres having a mean fibre diameter of between 1.9 to 2.6 microns, and wherein said fibres comprise over 95% glycolide.
2. A scaffold according to claim 1, wherein the fibre comprises over 90% polymer.
3. A scaffold according to claim 2, wherein the fibre comprises over 95% polymer.
4. A scaffold according to claim 2, wherein the fibre consists of 100% polymer.
5. A scaffold according to claim 2, wherein the polymer consists of 100% glycolide.
6. A scaffold according to claim 1, wherein the glycolide is polyglycolic acid.
7. A scaffold according to claim 1, wherein the fibre comprises a copolymer of a glycolide and a hydroxy acid.
8. A scaffold according to claim 7, wherein the hydroxy acid is a lactide.
9. A scaffold according to claim 8, wherein the co-polymer is poly(lactide-co-glycolide).
10. A scaffold according to claim 1, wherein the scaffold is a non-woven.
11. A scaffold according to claim 1, wherein the fibres are electrospun.
12. A medical dressing comprising a scaffold comprising fibres having a mean fibre diameter of between 1.9 to 2.6 microns, and wherein said fibres comprise over 95% glycolide.
13. A medical dressing according to claim 12, wherein the dressing is a wound dressing.
14. A medical dressing according to claim 12, wherein the fibre comprises over 90% polymer.
15. A medical dressing according to claim 12, wherein the glycolide is polyglycolic acid.
16. A medical dressing according to claim 12, wherein the fibre comprises a copolymer of a glycolide and a hydroxy acid.
17. A medical dressing according to claim 16, wherein the hydroxy acid is a lactide.
18. A medical dressing according to claim 17, wherein the co-polymer is poly(lactide-co-glycolide).
19. A medical dressing according to claim 12, wherein the scaffold is a non-woven.
20. A medical dressing according to claim 12, wherein the fibres are electrospun.

* * * * *

UNITED STATES PATENT AND TRADEMARK OFFICE
CERTIFICATE OF CORRECTION

PATENT NO.         : 8,338,402 B2
APPLICATION NO.    : 12/300636
DATED              : December 25, 2012
INVENTOR(S)        : Fry et al.

It is certified that error appears in the above-identified patent and that said Letters Patent is hereby corrected as shown below:

On title page 2, col. 1, item [56] at line 69, Under Other Publications, change "Apr. 15, 2004, Weston." to --Mar. 26, 2009, Greener et al.--.

On title page 2, col. 2, item [56] at line 17, Under Other Publications, change "Absorable" to --Absorbable--.

On title page 2, col. 2, item [56] at line 18, Under Other Publications, change "Obsterics" to --Obstetrics--.

On title page 2, col. 2, item [56] at line 35, Under Other Publications, change "Versative" to --Versatile--.

In the Specification

In column 1 at line 7, change "001713filled" to --001713 filled--.

In column 1 at line 38, change "biodegradability[1]" to --biodegradability--.

In column 2 at line 6, change "pare" to --pore--.

In column 3 at line 56, change "polyamids," to --polyamides,--.

In column 5 at line 19-23 (approx.), After

"PDLA + 20% PCL                                          83 ± 0 poly(D,L-lactic acid) = PDLA
poly(lactide-co-glycolide = PLGA
poly(ε-caprolactone) = PCL
polyglycolic acid = PGA delete " poly(L-lactide) = PLLA                            ".

In column 11 at line 50, change "20 vm" to --20 μm--.

Signed and Sealed this
Twenty-ninth Day of October, 2013

Teresa Stanek Rea
*Deputy Director of the United States Patent and Trademark Office*

In column 14 at line 61, change "(Beckman Coulter Ac.T 5 diff. Counter)." to --(Coulter® Ac-T™ 5diff. Counter).--.